United States Patent [19]
Peukert et al.

[11] Patent Number: 6,160,091
[45] Date of Patent: Dec. 12, 2000

[54] MYC-BINDING ZINC FINGER PROTEINS, THEIR PREPARATION AND THEIR USE

[75] Inventors: Karen Peukert, Lahntal-Sterzhausen; Frank Haenel, Jena; Martin Eilers, Marburg-Cappel, all of Germany

[73] Assignee: Prolifix Limited, United Kingdom

[21] Appl. No.: 09/063,035

[22] Filed: Apr. 21, 1998

[30] Foreign Application Priority Data

Apr. 30, 1997 [DE] Germany .................... 197 18 249

[51] Int. Cl.$^7$ .................................................. C07K 14/47
[52] U.S. Cl. ............................................ 530/350; 539/358
[58] Field of Search .................................. 530/350, 358, 530/400

[56] References Cited

PUBLICATIONS

Peukert et al. An alternative pathway for gene regulation by Myc. EMBO J. 16(18):5672–5686, Sep. 15, 1997.
Wells. Additivity of mutational effects in proteins. Biochemistry 29(37):8509–8517, Sep. 18, 1990.
Bowie et al. Deciphering the message in protein sequences: tolerance to amino acid substitutions. Science 247: 1306–1310, Mar. 16, 1990.
The Merck Index, Eighth Edition. Stecher et al, eds. Rahway: Merck & Co. p. 497, 1968.
Blackwood et al. Max: A helix–loop–helix zipper protein that forms a sequence specific DNA–binding complex with Myc. Science 251:12111217, Mar. 8, 1991.
Tommerup et al., Genomics, 27, 259–264, 1995.
Phillip et al., *Molecular and Cellular Biology*, 14(6), Jun. 1994, 4032–4043.
Schneider et al., *Current Topics In Microbiology and Immunology*, 224, 1997, 137–146.
Cell., vol. 56, 777–783, Mar. 10, 1989, Murre et al.
Cell., vol. 72, 233–245, Jan. 29, 1993, Amati et al.
Science, Jun. 24, 1988, 1759–1763, vol. 240, Landschulz et al.
Biochem. J. (1995) 311,219–224, Schulz et al.

*Primary Examiner*—Christopher S. F. Low
*Assistant Examiner*—Gabriele E. Bugaisky
*Attorney, Agent, or Firm*—Keil & Weinkauf

[57] ABSTRACT

Novel Myc-binding zinc finger proteins, their preparation and their use are provided.

2 Claims, No Drawings

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 2680 base pairs
      (B) TYPE: Nucleic acid
      (C) STRANDEDNESS: single
      (D) TOPOLOGY: linear (ii) MOLECULE TYPE: cDNA to mRNA -continued

```
     (iii) HYPOTHETICAL: NO (iv) ANTI-SENSE: NO (ix) FEATURE:
           (A) NAME/KEY: 5'UTR
           (B) LOCATION: 1..159

(ix) FEATURE:
           (A) NAME/KEY: CDS
           (B) LOCATION: 160..2571

(ix) FEATURE:
           (A) NAME/KEY: CDS
           (B) LOCATION: 2572..2680

(xi) SEQUENCE DESCRIPTION: SEQ ID NO: 1:

GGAGTGCCGT CCCCGGCCTT CTCGCGGCCG TGATGCACCT CCCTCTGCGG TGGGGTCCGG      60

GACATGGCAG GTAATGAGCC GGACGAGGGG AGCCAAGCTG GAGTTTACAC AGGCAAACTG     120

TCAGAAAAGA GTAGCCTGGG CTGTCTGGAA ATCTGAGCC ATG GAC TTT CCC CAG        174
                                             Met Asp Phe Pro Gln
                                              1               5

CAC AGC CAG CAT GTC TTG GAA CAG CTG AAC CAG CAG CGG CAG CTG GGG       222
His Ser Gln His Val Leu Glu Gln Leu Asn Gln Gln Arg Gln Leu Gly
             10                  15                  20

CTT CTC TGT GAC TGC ACC TTT GTG GTG GAC GGT GTT CAC TTT AAG GCT       270
Leu Leu Cys Asp Cys Thr Phe Val Val Asp Gly Val His Phe Lys Ala
         25                  30                  35

CAT AAA GCA GTG CTG GCG GCC TGC AGC GAG TAC TTC AAG ATG CTC TTC       318
His Lys Ala Val Leu Ala Ala Cys Ser Glu Tyr Phe Lys Met Leu Phe
     40                  45                  50

GTG GAC CAG AAG GAC GTG GTG CAC CTG GAC ATC AGT AAC GCG GCA GGC       366
Val Asp Gln Lys Asp Val Val His Leu Asp Ile Ser Asn Ala Ala Gly
 55                  60                  65

CTG GGG CAG ATG CTG GAG TTT ATG TAC ACG GCC AAG CTG AGC CTG AGC       414
Leu Gly Gln Met Leu Glu Phe Met Tyr Thr Ala Lys Leu Ser Leu Ser
 70                  75                  80                  85

CCT GAG AAC GTG GAT GAT GTG CTG GCC GTG GCC ACT TTC CTC CAA ATG       462
Pro Glu Asn Val Asp Asp Val Leu Ala Val Ala Thr Phe Leu Gln Met
                 90                  95                 100

CAG GAC ATC ATC ACG GCC TGC CAT GCC CTC AAG TCA CTT GCT GAG CCG       510
Gln Asp Ile Ile Thr Ala Cys His Ala Leu Lys Ser Leu Ala Glu Pro
            105                 110                 115

GCT ACC AGC CCT GGG GGA AAT GCG GAG GCC TTG GCC ACA GAA GGA GGG       558
Ala Thr Ser Pro Gly Gly Asn Ala Glu Ala Leu Ala Thr Glu Gly Gly
        120                 125                 130

GAC AAG AGA GCC AAA GAG GAG AAG GTG GCC ACC AGC ACG CTG AGC AGG       606
Asp Lys Arg Ala Lys Glu Glu Lys Val Ala Thr Ser Thr Leu Ser Arg
    135                 140                 145

CTG GAG CAG GCA GGA CGC AGC ACA CCC ATA GGC CCC AGC AGG GAC CTC       654
Leu Glu Gln Ala Gly Arg Ser Thr Pro Ile Gly Pro Ser Arg Asp Leu
150                 155                 160                 165

AAG GAG GAG CGC GGC GGT CAG GCC CAG AGT GCG GCC AGC GGT GCA GAG       702
Lys Glu Glu Arg Gly Gly Gln Ala Gln Ser Ala Ala Ser Gly Ala Glu
                170                 175                 180

CAG ACA GAG AAA GCC GAT GCG CCC CGG GAG CCG CCG CCT GTG GAG CTC       750
Gln Thr Glu Lys Ala Asp Ala Pro Arg Glu Pro Pro Pro Val Glu Leu
            185                 190                 195

AAG CCA GAC CCC ACG AGT GGC ATG GCT GCC GCA GAA GCT GAG GCC GCT       798
Lys Pro Asp Pro Thr Ser Gly Met Ala Ala Ala Glu Ala Glu Ala Ala
        200                 205                 210

TTG TCC GAG AGC TCG GAG CAA GAA ATG GAG GTG GAG CCC GCC CGG AAA       846
```

```
Leu Ser Glu Ser Ser Glu Gln Glu Met Glu Val Glu Pro Ala Arg Lys
    215                 220                 225

GGG GAA GAG GAG CAA AAG GAG CAA GAG GAG CAA GAG GAG GAG GGC GCA         894
Gly Glu Glu Glu Gln Lys Glu Gln Glu Glu Gln Glu Glu Glu Gly Ala
230                 235                 240                 245

GGG CCA GCT GAG GTC AAG GAG GAG GGT TCC CAG CTG GAG AAC GGA GAG         942
Gly Pro Ala Glu Val Lys Glu Glu Gly Ser Gln Leu Glu Asn Gly Glu
                250                 255                 260

GCC CCC GAG GAG AAC GAG AAT GAG GAG TCA GCG GGC ACA GAC TCG GGG         990
Ala Pro Glu Glu Asn Glu Asn Glu Glu Ser Ala Gly Thr Asp Ser Gly
            265                 270                 275

CAG GAG CTC GGC TCC GAG GCC CGG GGC CTG CGC TCA GGC ACC TAC GGC        1038
Gln Glu Leu Gly Ser Glu Ala Arg Gly Leu Arg Ser Gly Thr Tyr Gly
        280                 285                 290

GAC CGC ACG GAG TCC AAG GCC TAC GGC TCC GTC ATC CAC AAG TGC GAG        1086
Asp Arg Thr Glu Ser Lys Ala Tyr Gly Ser Val Ile His Lys Cys Glu
    295                 300                 305

GAC TGT GGG AAG GAG TTC ACG CAC ACG GGG AAC TTC AAG CGG CAC ATC        1134
Asp Cys Gly Lys Glu Phe Thr His Thr Gly Asn Phe Lys Arg His Ile
310                 315                 320                 325

CGC ATC CAC ACG GGG GAG AAG CCC TTC TCG TGC CGG GAG TGC AGC AAG        1182
Arg Ile His Thr Gly Glu Lys Pro Phe Ser Cys Arg Glu Cys Ser Lys
                330                 335                 340

GCC TTT TCC GAC CCG GCC GCG TGC AAG GCC CAT GAG AAG ACG CAC AGC        1230
Ala Phe Ser Asp Pro Ala Ala Cys Lys Ala His Glu Lys Thr His Ser
                345                 350                 355

CCT CTG AAG CCC TAC GGC TGC GAG GAG TGC GGG AAG AGC TAC CGC CTC        1278
Pro Leu Lys Pro Tyr Gly Cys Glu Glu Cys Gly Lys Ser Tyr Arg Leu
        360                 365                 370

ATC AGC CTG CTG AAC CTG CAC AAG AAG CGG CAC TCG GGC GAG GCG CGC        1326
Ile Ser Leu Leu Asn Leu His Lys Lys Arg His Ser Gly Glu Ala Arg
    375                 380                 385

TAC CGC TGC GAG GAC TGC GGC AAG CTC TTC ACC ACC TCG GGC AAC CTC        1374
Tyr Arg Cys Glu Asp Cys Gly Lys Leu Phe Thr Thr Ser Gly Asn Leu
390                 395                 400                 405

AAG CGC CAC CAG CTG GTG CAC AGC GGC GAG AAG CCC TAC CAG TGC GAC        1422
Lys Arg His Gln Leu Val His Ser Gly Glu Lys Pro Tyr Gln Cys Asp
                410                 415                 420

TAC TGC GGC CGC TCC TTC TCC GAC CCC ACT TCC AAG ATG CGC CAC CTG        1470
Tyr Cys Gly Arg Ser Phe Ser Asp Pro Thr Ser Lys Met Arg His Leu
                425                 430                 435

GAG ACC CAC GAC ACG GAC AAG GAG CAC AAG TGC CCA CAC TGC GAC AAG        1518
Glu Thr His Asp Thr Asp Lys Glu His Lys Cys Pro His Cys Asp Lys
        440                 445                 450

AAG TTC AAC CAG GTA GGG AAC CTG AAG GCC CAC CTG AAG ATC CAC ATC        1566
Lys Phe Asn Gln Val Gly Asn Leu Lys Ala His Leu Lys Ile His Ile
455                 460                 465

GCT GAC GGG CCC CTC AAG TGC CGA GAG TGT GGG AAG CAG TTC ACC ACC        1614
Ala Asp Gly Pro Leu Lys Cys Arg Glu Cys Gly Lys Gln Phe Thr Thr
470                 475                 480                 485

TCA GGG AAC CTG AAG CGG CAA CTT CGG ATC CAC AGC GGG GAG AAG CCC        1662
Ser Gly Asn Leu Lys Arg Gln Leu Arg Ile His Ser Gly Glu Lys Pro
                490                 495                 500

TAC GTG TGC ATC CAC TGC CAG CGA CAG TTT GCA GAC CCC GGC GCT CTG        1710
Tyr Val Cys Ile His Cys Gln Arg Gln Phe Ala Asp Pro Gly Ala Leu
                505                 510                 515

CAG CGG CAC GTC CGC ATT CAC ACA GGT GAG AAG CCA TGC CAG TGT GTG        1758
Gln Arg His Val Arg Ile His Thr Gly Glu Lys Pro Cys Gln Cys Val
        520                 525                 530
```

```
ATG TGC GGT AAG GCC TTC ACC CAG GCC AGC TCC CTC ATC GCC CAC GTG       1806
Met Cys Gly Lys Ala Phe Thr Gln Ala Ser Ser Leu Ile Ala His Val
    535                 540                 545

CGC CAG CAC ACC GGG GAG AAG CCC TAC GTC TGC GAG CGC TGC GGC AAG       1854
Arg Gln His Thr Gly Glu Lys Pro Tyr Val Cys Glu Arg Cys Gly Lys
550                 555                 560                 565

AGA TTC GTC CAG TCC AGC CAG TTG GCC AAT CAT ATT CGC CAC CAC GAC       1902
Arg Phe Val Gln Ser Ser Gln Leu Ala Asn His Ile Arg His His Asp
                570                 575                 580

AAC ATC CGC CCA CAC AAG TGC AGC GTG TGC AGC AAG GCC TTC GTG AAC       1950
Asn Ile Arg Pro His Lys Cys Ser Val Cys Ser Lys Ala Phe Val Asn
            585                 590                 595

GTG GGG GAC CTG TCC AAG CAC ATC ATC ATT CAC ACT GGA GAG AAG CCT       1998
Val Gly Asp Leu Ser Lys His Ile Ile Ile His Thr Gly Glu Lys Pro
        600                 605                 610

TAC CTG TGT GAT AAG TGT GGG CGT GGC TTC AAC CGG GTA GAC AAC CTG       2046
Tyr Leu Cys Asp Lys Cys Gly Arg Gly Phe Asn Arg Val Asp Asn Leu
    615                 620                 625

CGC TCC CAC GTG AAG ACC GTG CAC CAG GGC AAG GCA GGC ATC AAG ATC       2094
Arg Ser His Val Lys Thr Val His Gln Gly Lys Ala Gly Ile Lys Ile
630                 635                 640                 645

CTG GAG CCC GAG GAG GGC AGT GAG GTC AGC GTG GTC ACT GTG GAT GAC       2142
Leu Glu Pro Glu Glu Gly Ser Glu Val Ser Val Val Thr Val Asp Asp
                650                 655                 660

ATG GTC ACG CTG GCT ACC GAG GCA CTG GCA GCG ACA GCC GTC ACT CAG       2190
Met Val Thr Leu Ala Thr Glu Ala Leu Ala Ala Thr Ala Val Thr Gln
            665                 670                 675

CTC ACA GTG GTG CCG GTG GGA GCT GCA GTG ACA GCC GAT GAG ACG GAA       2238
Leu Thr Val Val Pro Val Gly Ala Ala Val Thr Ala Asp Glu Thr Glu
        680                 685                 690

GTC CTG AAG GCC GAG ATC AGC AAA GCT GTG AAG CAA GTG CAG GAA GAA       2286
Val Leu Lys Ala Glu Ile Ser Lys Ala Val Lys Gln Val Gln Glu Glu
    695                 700                 705

GAC CCC AAC ACT CAC ATC CTC TAC GCC TGT GAC TCC TGT GGG GAC AAG       2334
Asp Pro Asn Thr His Ile Leu Tyr Ala Cys Asp Ser Cys Gly Asp Lys
710                 715                 720                 725

TTT CTG GAT GCC AAC AGC CTG GCT CAG CAT GTG CGA ATC CAC ACA GCC       2382
Phe Leu Asp Ala Asn Ser Leu Ala Gln His Val Arg Ile His Thr Ala
                730                 735                 740

CAG GCA CTG GTC ATG TTC CAG ACA GAC GCG GAC TTC TAT CAG CAG TAT       2430
Gln Ala Leu Val Met Phe Gln Thr Asp Ala Asp Phe Tyr Gln Gln Tyr
            745                 750                 755

GGG CCA GGT GGC ACG TGG CCT GCC GGG CAG GTG CTG CAG GCT GGG GAG       2478
Gly Pro Gly Gly Thr Trp Pro Ala Gly Gln Val Leu Gln Ala Gly Glu
        760                 765                 770

CTG GTC TTC CGC CCT CGC GAC GGG GCT GAG GGC CAG CCC GCA CTG GCA       2526
Leu Val Phe Arg Pro Arg Asp Gly Ala Glu Gly Gln Pro Ala Leu Ala
    775                 780                 785

GAG ACC TCC CCT ACA CCT CCT GAA TGT CCC CCG CCT GCC GAG TGAGCTGGCG   2578
Glu Thr Ser Pro Thr Pro Pro Glu Cys Pro Pro Pro Ala Glu
790                 795                 800

GCCCTTCTGA CTGTTTATTT AAGGATGGAT GGCACCCTGG AACCGGGAAG GGTGGCCTGT   2638

TCCCTAGAGA GAATAAATTG GATTATTTTC TAAAAAAAAA AA                      2680

(2) INFORMATION FOR SEQ ID NO: 2:

(i) SEQUENCE CHARACTERISTICS:
        (A) LENGTH: 803 amino acids
        (B) TYPE: amino acid
        (D) TOPOLOGY: linear
```

(xi) SEQUENCE DESCRIPTION: SEQ ID NO: 2:

```
Met Asp Phe Pro Gln His Ser Gln His Val Leu Glu Gln Leu Asn Gln
 1               5                  10                  15

Gln Arg Gln Leu Gly Leu Leu Cys Asp Cys Thr Phe Val Val Asp Gly
            20                  25                  30

Val His Phe Lys Ala His Lys Ala Val Leu Ala Ala Cys Ser Glu Tyr
        35                  40                  45

Phe Lys Met Leu Phe Val Asp Gln Lys Asp Val Val His Leu Asp Ile
    50                  55                  60

Ser Asn Ala Ala Gly Leu Gly Gln Met Leu Glu Phe Met Tyr Thr Ala
65                  70                  75                  80

Lys Leu Ser Leu Ser Pro Glu Asn Val Asp Asp Val Leu Ala Val Ala
                85                  90                  95

Thr Phe Leu Gln Met Gln Asp Ile Ile Thr Ala Cys His Ala Leu Lys
            100                 105                 110

Ser Leu Ala Glu Pro Ala Thr Ser Pro Gly Gly Asn Ala Glu Ala Leu
        115                 120                 125

Ala Thr Glu Gly Gly Asp Lys Arg Ala Lys Glu Glu Lys Val Ala Thr
    130                 135                 140

Ser Thr Leu Ser Arg Leu Glu Gln Ala Gly Arg Ser Thr Pro Ile Gly
145                 150                 155                 160

Pro Ser Arg Asp Leu Lys Glu Glu Arg Gly Gly Gln Ala Gln Ser Ala
                165                 170                 175

Ala Ser Gly Ala Glu Gln Thr Glu Lys Ala Asp Ala Pro Arg Glu Pro
            180                 185                 190

Pro Pro Val Glu Leu Lys Pro Asp Pro Thr Ser Gly Met Ala Ala Ala
        195                 200                 205

Glu Ala Glu Ala Leu Ser Glu Ser Ser Gln Glu Met Glu Val
    210                 215                 220

Glu Pro Ala Arg Lys Gly Glu Glu Gln Lys Glu Gln Glu Glu Gln
225                 230                 235                 240

Glu Glu Glu Gly Ala Gly Pro Ala Glu Val Lys Glu Glu Gly Ser Gln
                245                 250                 255

Leu Glu Asn Gly Glu Ala Pro Glu Glu Asn Glu Asn Glu Glu Ser Ala
            260                 265                 270

Gly Thr Asp Ser Gly Gln Glu Leu Gly Ser Glu Ala Arg Gly Leu Arg
        275                 280                 285

Ser Gly Thr Tyr Gly Asp Arg Thr Glu Ser Lys Ala Tyr Gly Ser Val
    290                 295                 300

Ile His Lys Cys Glu Asp Cys Gly Lys Glu Phe Thr His Thr Gly Asn
305                 310                 315                 320

Phe Lys Arg His Ile Arg Ile His Thr Gly Glu Lys Pro Phe Ser Cys
                325                 330                 335

Arg Glu Cys Ser Lys Ala Phe Ser Asp Pro Ala Ala Cys Lys Ala His
            340                 345                 350

Glu Lys Thr His Ser Pro Leu Lys Pro Tyr Gly Cys Glu Glu Cys Gly
        355                 360                 365

Lys Ser Tyr Arg Leu Ile Ser Leu Leu Asn Leu His Lys Lys Arg His
    370                 375                 380

Ser Gly Glu Ala Arg Tyr Arg Cys Glu Asp Cys Gly Lys Leu Phe Thr
385                 390                 395                 400

Thr Ser Gly Asn Leu Lys Arg His Gln Leu Val His Ser Gly Glu Lys
```

-continued

```
            405                 410                 415
Pro Tyr Gln Cys Asp Tyr Cys Gly Arg Ser Phe Ser Asp Pro Thr Ser
                420                 425                 430

Lys Met Arg His Leu Glu Thr His Asp Thr Asp Lys Glu His Lys Cys
            435                 440                 445

Pro His Cys Asp Lys Lys Phe Asn Gln Val Gly Asn Leu Lys Ala His
        450                 455                 460

Leu Lys Ile His Ile Ala Asp Gly Pro Leu Lys Cys Arg Glu Cys Gly
465                 470                 475                 480

Lys Gln Phe Thr Thr Ser Gly Asn Leu Lys Arg Gln Leu Arg Ile His
                485                 490                 495

Ser Gly Glu Lys Pro Tyr Val Cys Ile His Cys Gln Arg Gln Phe Ala
            500                 505                 510

Asp Pro Gly Ala Leu Gln Arg His Val Arg Ile His Thr Gly Glu Lys
        515                 520                 525

Pro Cys Gln Cys Val Met Cys Gly Lys Ala Phe Thr Gln Ala Ser Ser
530                 535                 540

Leu Ile Ala His Val Arg Gln His Thr Gly Glu Lys Pro Tyr Val Cys
545                 550                 555                 560

Glu Arg Cys Gly Lys Arg Phe Val Gln Ser Ser Gln Leu Ala Asn His
                565                 570                 575

Ile Arg His His Asp Asn Ile Arg Pro His Lys Cys Ser Val Cys Ser
            580                 585                 590

Lys Ala Phe Val Asn Val Gly Asp Leu Ser Lys His Ile Ile Ile His
        595                 600                 605

Thr Gly Glu Lys Pro Tyr Leu Cys Asp Lys Cys Gly Arg Gly Phe Asn
610                 615                 620

Arg Val Asp Asn Leu Arg Ser His Val Lys Thr Val His Gln Gly Lys
625                 630                 635                 640

Ala Gly Ile Lys Ile Leu Glu Pro Glu Gly Ser Glu Val Ser Val
                645                 650                 655

Val Thr Val Asp Asp Met Val Thr Leu Ala Thr Glu Ala Leu Ala Ala
            660                 665                 670

Thr Ala Val Thr Gln Leu Thr Val Val Pro Val Gly Ala Ala Val Thr
        675                 680                 685

Ala Asp Glu Thr Glu Val Leu Lys Ala Glu Ile Ser Lys Ala Val Lys
690                 695                 700

Gln Val Gln Glu Glu Asp Pro Asn Thr His Ile Leu Tyr Ala Cys Asp
705                 710                 715                 720

Ser Cys Gly Asp Lys Phe Leu Asp Ala Asn Ser Leu Ala Gln His Val
                725                 730                 735

Arg Ile His Thr Ala Gln Ala Leu Val Met Phe Gln Thr Asp Ala Asp
            740                 745                 750

Phe Tyr Gln Gln Tyr Gly Pro Gly Gly Thr Trp Pro Ala Gly Gln Val
        755                 760                 765

Leu Gln Ala Gly Glu Leu Val Phe Arg Pro Arg Asp Gly Ala Glu Gly
770                 775                 780

Gln Pro Ala Leu Ala Glu Thr Ser Pro Thr Pro Pro Glu Cys Pro Pro
785                 790                 795                 800

Pro Ala Glu
```

MYC-BINDING ZINC FINGER PROTEINS, THEIR PREPARATION AND THEIR USE

The present invention relates to Myc binding zinc finger proteins, to their preparation and to their use.

Myc is a protein which specifically binds to DNA. It belongs to the family of helix-loop-helix/leucine zipper (HLH/LZ) transcription factors (Landschulz et al., 1998, Murre et al., 1989). Myc is a central transcription activator which forms a complex with the protein Max (Amati et al., 1993) and, by this molecular mechanism, activates other genes, for example the alpha-prothymosine gene, the ornithine decarboxylase gene and cdc25A.

Schulz et al., 1995, described a mouse protein which contains 13 zinc fingers but whose cellular function is unclear.

Because of its key position in transcription, Myc provides a starting point for understanding cellular, in particular pathophysiological, processes.

It is an object of the present invention to provide further information about the molecular mode of action of Myc, in particular about the gene repression mediated by Myc.

The invention relates to a protein having the amino acid sequence depicted in SEQ ID NO:2. This protein has thirteen zinc finger domains.

It has the following biological properties:
specific binding to Myc,
transactivation of the adenovirus major late (AdML) promoter,
transactivation of the cyclin D1 promoter,
transactivation is inhibited by association with Myc,
in the absence of Myc, the protein is to be found essentially in the cytosol associated with microtubules.

The invention furthermore relates to proteins derived from the structure depicted in SEQ ID NO:2 by substitution, insertion or deletion of one or more amino acids, these proteins still having the essential biological properties of the protein described by SEQ ID NO:2. These proteins are referred to as muteins hereinafter. Essential properties include the specific binding of the muteins to Myc.

The abovementioned properties of the protein described by SEQ ID NO:2 need not all be present in the muteins as long as the specific binding to Myc is. However, the muteins which have all the abovementioned properties are preferred.

The number of amino acids altered by insertion, substitution or deletion by comparison with the protein described by SEQ ID NO:2 may vary from 1 to 100, preferably from 1 to 50, amino acids.

The alterations may be concentrated in a relatively small area of the molecule or else be distributed over the entire molecule.

Preferred alterations are conservative substitutions in which one amino acid is replaced by another amino acid with a similar bulk, charge or hydrophilicity.

Examples of such conservative substitutions are
replacement of Arg by Lys or vice versa,
replacement of Arg by His or vice versa,
replacement of Asp by Glu or vice versa,
replacement of Asn by Gln or vice versa,
replacement of Cys by Met or vice versa,
replacement of Cys by Ser or vice versa,
replacement of Gly by Ala or vice versa,
replacement of Val by Leu or vice versa,
replacement of Val by Ile or vice versa,
replacement of Leu by Ile or vice versa,
replacement of Phe by Tyr or vice versa,
replacement of Phe by Trp or vice versa,
replacement of Ser by Thr or vice versa.

The alterations may also be combined, eg. one or more substitutions with deletions and/or insertions.

The invention further relates to nucleic acid sequences which code for the proteins described above. These nucleic acid sequences are preferably DNA, in particular cDNA, sequences in single-stranded or double-stranded form.

Preferred nucleic acid sequences are those having the sequence depicted in SEQ ID NO:1 and those having a high degree of relationship with this sequence, for example those which code for the same protein as SEQ ID NO:1. Further preferred nucleic acid sequences are those which code for a protein which has 95% or more identity to the protein of sequence SEQ ID NO:2.

The invention further relates to vectors which harbor one of the nucleic acid sequences described above in functional linkage to one or more regulatory elements. Regulatory elements mean nucleic acid fragments which have a controlling effect on transcription or translation, for example promoters, enhancers, polyadenylation sites and ribosome binding sites.

The invention likewise relates to host organisms transformed with vectors of this type. Suitable host organisms are microorganisms, plant or animal cells or living things. Preferred host organisms are eukaryotic cells and living things. The term host organism also includes, for example, transgenic animals and plants.

The proteins according to the invention are preferably prepared with the aid of genetic engineering processes. A host organism which harbors the genetic information for the proteins according to the invention is cultivated under conditions which permit expression of the protein. These conditions, such as temperature, nutrient medium, cell density, substantially depend on the choice of the host organism. However, the skilled worker is aware of such conditions for individual host organisms.

The expressed proteins are subsequently, where appropriate after disruption of the host organism, separated from the host organism and isolated in pure form by known methods of protein purification, such as precipitation, chromatography, electrophoresis. The invention further relates to the use of the proteins as antigen to produce antibodies, and to the antibodies obtained in this way. Polyclonal antisera or else monoclonal antibodies can be prepared by processes known to the skilled worker.

The proteins according to the invention are also suitable as test systems for finding potential selective transcription-modulating substances. This can be tested particularly well by utilizing the ability of the proteins to form a protein complex with Myc. The invention therefore further relates to a method for identifying specific transcription-modulating substances which comprises the following steps:

(a) Incubating the protein as claimed in claim 1 with the myc gene product under conditions such that a complex between these two proteins is formed, (b) incubating the two proteins in the presence of one or more substances which are to be tested for specific transcription-modulating activities but under conditions which are otherwise the same as in (a), (c) determining the difference in the protein complex formation between (b) and (a), (d) selecting those substances with which the protein complex formation in step (b) is different from that in step (a).

It is possible thereby to find substances which promote complex formation between the novel zinc finger protein and Myc, but also those which suppress it.

The nucleic acid sequences according to the invention are also suitable for gene therapy of diseases in which the transcription mediated by Myc is deranged.

For example, additional gene sequences can be introduced in order, in this way, to increase the cellular concentration of the zinc finger proteins. However, it may also be desirable to decrease the concentration of the zinc finger proteins. In this case, an antisense-based gene therapy is suitable, in which case a nucleic acid or nucleic acid derivative complementary to the zinc finger protein gene is administered, and thus expression of the zinc finger protein gene is reduced.

Further development of the invention is described in the following examples.

EXAMPLE 1
Isolation of the DNA Having the Structure Described by SEQ ID NO:1

Previous work had shown that the integrity of the helix-loop-helix domain of Myc was critical for gene repression by Myc in stable cell lines (Philipp et al., 1994). In order to identify novel proteins which interact with the C terminus of Myc, a DNA fragment which codes for the basic region and the HLH/LZ domain (amino acids 355-439 of human Myc) was fused in reading frame to the DNA-binding domain of GAL4 (amino acid 1-147) and used as bait in a two-hybrid screen (Fields and Song, 1989).

$2 \times 10^5$ independent transformants from a HeLa cDNA library, with the GAL4 activation domain as marker, were screened. One clone with β-galactosidase activity was characterized further. No interaction was found between the protein encoded by this clone and the DNA binding domain of GAL4 alone or of a GAL4-BCY-1 chimera which was used as negative control.

The interaction with Myc was abolished by deletion of the HLH domain in Myc (370-412) but not by insertion of the four amino acids between the HLH domain and the leucine zipper (In 412) or by deletion of the complete leucine zipper (412-434). A specific interaction was also detected with N-Myc but not with MAX or USF, two HLH proteins which are closely related by Myc.

Full-length cDNA molecules were isolated by a 5'-RACE protocol and were sequenced (SEQ ID NO:1). They encode a protein having 803 amino acids (SEQ ID NO:2) with a theoretical molecular weight of 87.970 dalton. The protein was called Miz-1 for Myc-interacting zinc finger protein 1.

Sequencing revealed that the isolated clone coded for a zinc finger protein with 13 zinc fingers, 12 of them clustered directly in the C-terminal half of the protein.

EXAMPLE 2
Preparation of Muteins

It is possible, starting from the nucleic acid sequence depicted in SEQ ID NO:1, to prepare by genetic engineering methods familiar to the skilled worker nucleic acids which code for altered proteins (muteins). The muteins themselves are expediently prepared by expressing a nucleic acid in a suitable host organism.

EXAMPLE 3
Asosciation of the Protein of SEQ ID NO:2 with Myc.

The C terminus of the protein of SEQ ID NO:2 (amino acid 269-803) was fused to glutathione transferase (GST) (Smith and Johnson, 1988), and the GST-Miz-1 fusion protein was purified and incubated with in vitro synthesized, radiolabeled Myc protein. Myc associates specifically with GST-Miz-1 but not with GST. A mutant of Myc which lacks the HLH domain was unable to associate with GST-Miz-1. Radiolabeled Max interacts neither with GST-Miz-1 nor with GST. However, Max is able with the aid of Myc to bind to GST-Miz-1-beads in vitro, which indicates that Miz-1 and Max interact with different areas of the HLH domain of Myc.

LIST OF REFERENCES

Amati, B., Brooks, M. W., Levy, N., Littlewood, T. D., Evan, G. I., and Land, H. (1993). Oncogenic activity of the c-Myc protein requires dimerization with Max. Cell 72, 233–245.

Fields, S., and Song, O. (1989). A novel genetic system to detect protein-protein interactions. Nature 340, 245–246.

Landschulz, W. H., Johnson, P. F., and McKnight, S. L. (1988). The leucine zipper: a hypothetical structure common to a new class of DNA binding proteins. Science 240, 1759–1764.

Murre, C., SchonleberMcCaw, P., and Baltimore, D. (1989). A new DNA binding and dimerization motif in immunoglobulin enhancer binding, daughterless, MyoD, and Myc proteins. Cell 56, 777–783.

Philipp, A., Schneider, A., Väsrik, I., Finke, K., Xiong, Y., Beach, D., Alitalo, K., and Eilers, M. (1994). Repression of Cyclin D1: a Novel Function of MYC. Mol. Cell. Biol. 14, 4032–4043.

Schulz, T. C., Hopwood, B., Rathjen, P. D., and Wells, J. R. (1995). An unusual arrangement of 13 zinc fingers in the vertebrate gene z13. Biochem. J. 311, 219–224.

Smith, D. B., and Johnson, K. S. (1988). Single-step purification of polypeptides expressed in *Escherichia coli* as fusions with glutathione S-transferase. Gene 67, 31–40.

We claim:

1. An isolated myc-binding protein having the amino acid sequence depicted in SEQ ID NO:2.

2. The protein defined in claim 1, which is a human protein.

* * * * *